US011688262B1

(12) United States Patent
Trimnell

(10) Patent No.: US 11,688,262 B1
(45) Date of Patent: Jun. 27, 2023

(54) PATIENT POSITION MONITORING AND WARNING SYSTEM FOR DETECTING BODILY MOVEMENTS AND PREVENTING FALLS

(71) Applicant: Ralph Trimnell, Albuquerque, NM (US)

(72) Inventor: Ralph Trimnell, Albuquerque, NM (US)

( * ) Notice: Subject to any disclaimer, the term of this patent is extended or adjusted under 35 U.S.C. 154(b) by 0 days.

(21) Appl. No.: 18/099,927

(22) Filed: Jan. 21, 2023

(51) Int. Cl.
*G08B 23/00* (2006.01)
*G08B 21/04* (2006.01)
*A61B 5/11* (2006.01)
*A61B 5/00* (2006.01)

(52) U.S. Cl.
CPC .......... *G08B 21/0423* (2013.01); *A61B 5/002* (2013.01); *A61B 5/1115* (2013.01); *A61B 5/6802* (2013.01); *A61B 5/7405* (2013.01); *A61B 5/746* (2013.01); *G08B 21/0446* (2013.01); *A61B 2562/0219* (2013.01)

(58) Field of Classification Search
CPC ........................ G08B 21/0423; G08B 21/0446; A61B 5/002; A61B 5/1115; A61B 5/6802; A61B 5/7405; A61B 5/746; A61B 2562/0219
See application file for complete search history.

(56) References Cited

U.S. PATENT DOCUMENTS

| | | | |
|---|---|---|---|
| 9,607,498 B2* | 3/2017 | Osorio | A61B 5/389 |
| 2014/0276238 A1* | 9/2014 | Osorio | G08B 21/0446 600/595 |
| 2017/0150905 A1* | 6/2017 | Shen | A61B 5/1115 |
| 2018/0228405 A1* | 8/2018 | Burwinkle | A61B 5/7275 |

* cited by examiner

*Primary Examiner* — Toan N Pham
(74) *Attorney, Agent, or Firm* — Robert D. Watson

(57) ABSTRACT

A wearable, body position monitor and activity alert device, designed to protect patients with a compromised ability to stand or walk from their own impulses to stand up by delivering a personal audible message of "caution", "persuasion", "discouragement" and/or "direction" when detecting the initiation of a "signature body movement" that could lead to a dangerous fall. The objective is to prevent falls from happening by monitoring a person's movements using a 3D accelerometer sensor and/or a 3D gyroscope sensor. No caregiver assistance belts, tethers, or other restraints are needed. When the patient starts to stand up, the patient monitoring system simultaneously and wirelessly alerts a caregiver, who is wearing a Caregiver's Personal Alert Device (CPAD), of the patient's intent to stand. When alerted by the CPAD, the caregiver then intervenes before the patient falls.

20 Claims, 18 Drawing Sheets

Stages of Standing Up

Caregiver's Personal Alert Device (CPAD), 600

PATIENT POSITION MONITORING AND WARNING SYSTEM FOR DETECTING BODILY MOVEMENTS AND PREVENTING FALLS

CROSS-REFERENCE TO RELATED APPLICATIONS

None

TECHNICAL FIELD

These embodiments generally relate to wireless Patient Monitoring and Activity Alert (PMAA) and "Fall Alert" devices and methods for alerting a caregiver if a patient with dementia or Alzheimer's disease is initially starting to stand up from a seated or a horizontal lying down position.

BACKGROUND OF THE INVENTION

Many persons suffering from dementia, Alzheimer's disease, or other cognitive issues spend their days in their homes or in nursing homes sitting in wheelchairs, occasionally being moved from rehabilitation, to meals, to play Bingo™, or just sitting in hallways. Many are unable to stand or walk without caregiver help. Occasionally a patient may attempt to rise and walk. If that occurs when there is no attendant or caregiver nearby, the patient may fall and break a bone, which could result in additional disability. Patients with neurological and/or stability impairments residing safely in a seated or lying down position occasionally obey an impulse to get out of their chair or bed, rise, and walk (perhaps remembering an earlier normal existence). This impulse, if not reversed, may result in a fall; thereby entailing unnecessary pain, disability, and expense. Common preventive "Fall Alert" devices and methods depend on audible alarms that summon caregivers whose reaction time is dependent on a number of indeterminate factors. If the caregiver is located another room or building, the caregiver's reaction time may be too long, resulting in ineffective intervention and an undesirable patient fall. In addition, the nonspecific nature of the conventional "Fall Alert" alarms renders them ineffective in locating the patient or directly warning the patient and/or the caregiver. Accordingly, a need exists for a compact, wearable, and timely alert/response system specifically designed for this particular population. The use of verbal persuasion at the earliest possible moment of a patient's intent-to-stand is a valuable goal of the innovative devices and methods described in the present disclosure.

SUMMARY OF THE INVENTION

The Patient Monitoring and Activity Alert (PMAA) system and methods of use described herein comprise a wireless wearable notification device that detects patient movement before the patient gets up from a chair, or gets up from lying down in a bed, and then takes a fall. The systems and methods described herein deliver an audible message (e.g., a recorded "Suggestion", "Command" or "Alarm" message) to the patient, as an incentive to get him/her to sit or lay back down. The patient is not considered a passive vessel to be externally protected (such, as with restraints), but is an active participant in his/her own fate. The method includes a program space of an microcomputer program that records the patient's bodily motions as a series of spatial vectors forming a pattern that is stored in a local computer memory that is compared with new movements to improve the monitoring system's reliability and sensitivity. Because of this, no caregiver assistance belts, no tethers, or other restraints are used. This allows the PMAA monitoring system to be "restraint free" and more acceptable to the caregiver industry. The objective of using the PMAA device is to prevent falls from happening by monitoring a person's movements using miniaturized a 3D accelerometer sensor and/or a 3D gyroscopic sensor. This reduces stress on family caregivers who are taking care of their patients. When the patient starts to stand up, the monitoring system simultaneously and wirelessly alerts a Caregiver's Personal Alert Device (CPAD) of the patient's intent to stand, who can intervene before a fall occurs.

The various examples of devices described in the present disclosure can include one or more of the following three main features, and/or combinations and sub-combinations thereof:

1. An electronic mechanism that detects predictive changes in a patient's bodily orientation, rotation angle, and vertical position, which identifies a patient's early intent to stand up;
2. An audio recording and playback means for delivering an audible early-warning message to the patient to dissuade such action; and
3. Wireless means to simultaneous transmit the derived "intent-to-stand" condition (a signature movement event) to a remote Caregiver's Personal Alarm Device (CPAD).

Some examples of recorded messages can include the following sample messages, including combinations and sub-combinations thereof:
(1) "Hi, Bob. This is Mary. This is not a good time to stand up. Please sit down." [Suggestive];
(2) "Bob, sit down now!" [Persuasive Command]; and
(3) "Help me, I've fallen and I can't get up!!!" [Alarm].

An example of a basic method of use can include performing the following steps, in the order as presented below:
(1) Patient bends his/her upper body forward to a degree necessary to begin upward movement. Movement sensor(s) detect this "signature movement event";
(2) The PMAA sends a recorded "suggestion" message to the patient via an audio speaker located close to one ear;
(3) A simultaneous alarm is wirelessly sent to a remote Caregiver's Personal Alert Device (CPAD); and (4) If the patient continues to display this change in seated position or ultimately stands up, the audio message and the caregiver alarm are both repeated simultaneously, with an increase in volume each time.

Step #4 can be repeated as long as the "signature movement event" is present, or when a control switch in the CPAD is activated.

A repeated triggering of signals sent simultaneously to both warning devices (PMAA and CPAD) can represent an escalation of the severity of the signature movement event to both parties, which can be used to replace the use of a subsequent "command or alarm message", as previously described.

DETAILED DESCRIPTION OF THE INVENTION

Figure 1A:
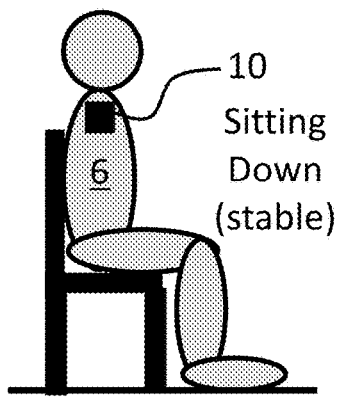
FIG. 1A shows a simplified diagram illustrating an example of a patient who is comfortably sitting in a chair, according to the present disclosure.

All publications, patient applications, patients, and other references mentioned herein are incorporated by reference in their entirety to the extent allowed by applicable law and regulations. The Patient Monitoring and Activity Alert (PMAA) device, Caregiver's Personal Alert Device (CPAD), and various methods of use described herein may be embodied in other specific forms without departing from the spirit or attributes thereof, and it is therefore desired that the present examples be considered in all respects as illustrative and not being restrictive. Any headings utilized within the present disclosure and/or contained in the Drawings are for convenience only and have no legal or limiting effect. The words "event", "signature event", "motion event", "movement event", and "signature movement event" are all interchangeable and refer to a predictable, preparatory situation where a patient telegraphs or indicates his/her intent to stand up from a chair or wheelchair, or his/her intent to start getting out of a bed. The words "alarm" and "alert" are used interchangeably in the present disclosure. The word "chip" refers to an Integrated Circuit (IC) semiconductor chip.

Processes and devices according to the present disclosure may be implemented and utilized for controlling a patient monitoring and activity alert (PMAA) system based on a microcomputer program. These processes and devices may be implemented and utilized, as will be explained next, with reference to various examples. Examples of the present disclosure includes devices and methods for reminding people with cognitive impairment who cannot stand or walk unaided. The system can comprise a recordable digital message device with audio output (e.g., a loudspeaker, headphones, earpiece, or hearing aid and/or combinations or sub-combinations thereof) preferably located at shoulder level; and one or more bodily position/movement sensors capable of determining the patient's position, rotational orientation, and upward movement. A compact, programmable PMAA computing device receives information from the one or more sensor(s) and determines by using programmed computer algorithms a decisive moment in time and movement space that signals that the patient is intending to rise to an upright position from a sitting or prone position. The system then plays an audible warning message, preferably comprising a personal recorded message from a caregiver, friend, or family member, or the patient himself/ herself, which suggests, persuades, cautions, and/or commands the patient to return to the original sitting or lying down position. Although any message may be used, I have discovered that a voice familiar to the patient, such as a close friend, relative, or caregiver, or the patient himself/herself, is most effective in reminding the patient to stop rising. The style and content of the audio message is one that is most likely to achieve the goal, and is preferably determined by those most familiar with the specific patient. The audio device supplied is preferably capable of quality audio reproduction sufficient to produce adequate discrimination of tones and speaking styles, so the patient can automatically recognize the speaker. If a common alarm sound is used instead of a friend's voice, the patient may then confuse the audible alarm with a telephone's ring sound, which may actually cause the patient to stand up and go to "answer the phone". At the same time the audio message is played, an alert or alarm signal is simultaneously sent wirelessly (e.g., using Bluetooth™ protocols) to a Caregiver's Personal Alert Device (CPAD). The CPAD can also provide an audible alarm or spoken message when it is triggered, as well as an optional LED alert lamp that can alternatively flash ON/OFF, or can stay permanently ON during the duration of a "signature movement event".

Figure 1B:
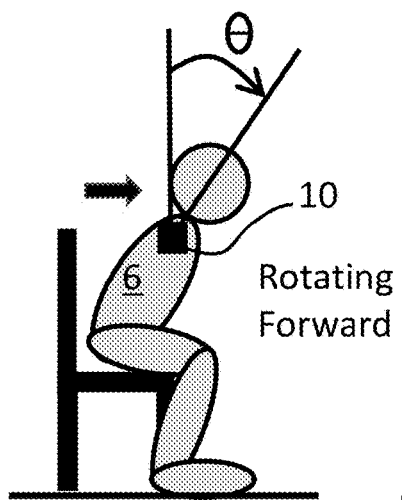
FIG. 1B shows a side view of a schematic diagram illustrating an example of a patient 6 who is starting to stand up by rotating his/her chest forward by an angle=theta, while still sitting a chair, according to the present disclosure.

FIG. 1A shows a side view of a schematic diagram illustrating an example of a patient 6 wearing a PMAA device 10 who is initially sitting comfortably in a chair or wheelchair (or bed, not shown), according to the present disclosure, FIG. 1B shows a side view of a schematic diagram illustrating an example of a patient 6 who is starting to stand up by rotating his/her chest forward by an angle=theta, while still sitting in a chair, according to the present disclosure. This movement places the patient's center of gravity over their feet, in preparation for standing up.

Figure 1C:
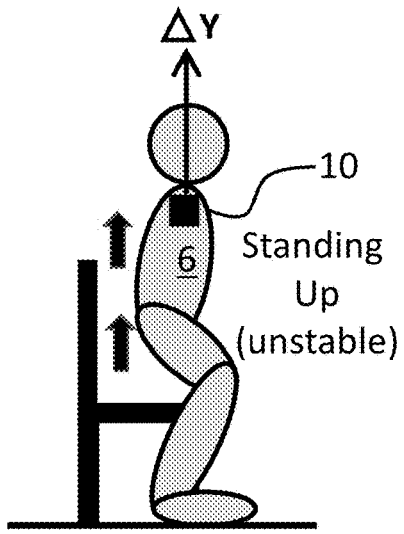
FIG. 1C shows a side view of a schematic diagram illustrating an example of a patient 6 who is in the process of standing up in a vertical direction by a vertical distance=delta-Y, according to the present disclosure.

FIG. 1C shows a side view of a schematic diagram illustrating an example of a patient 6 who is in the process of standing up in a vertical direction by a vertical distance=delta-Y, according to the present disclosure.

Figure 2:
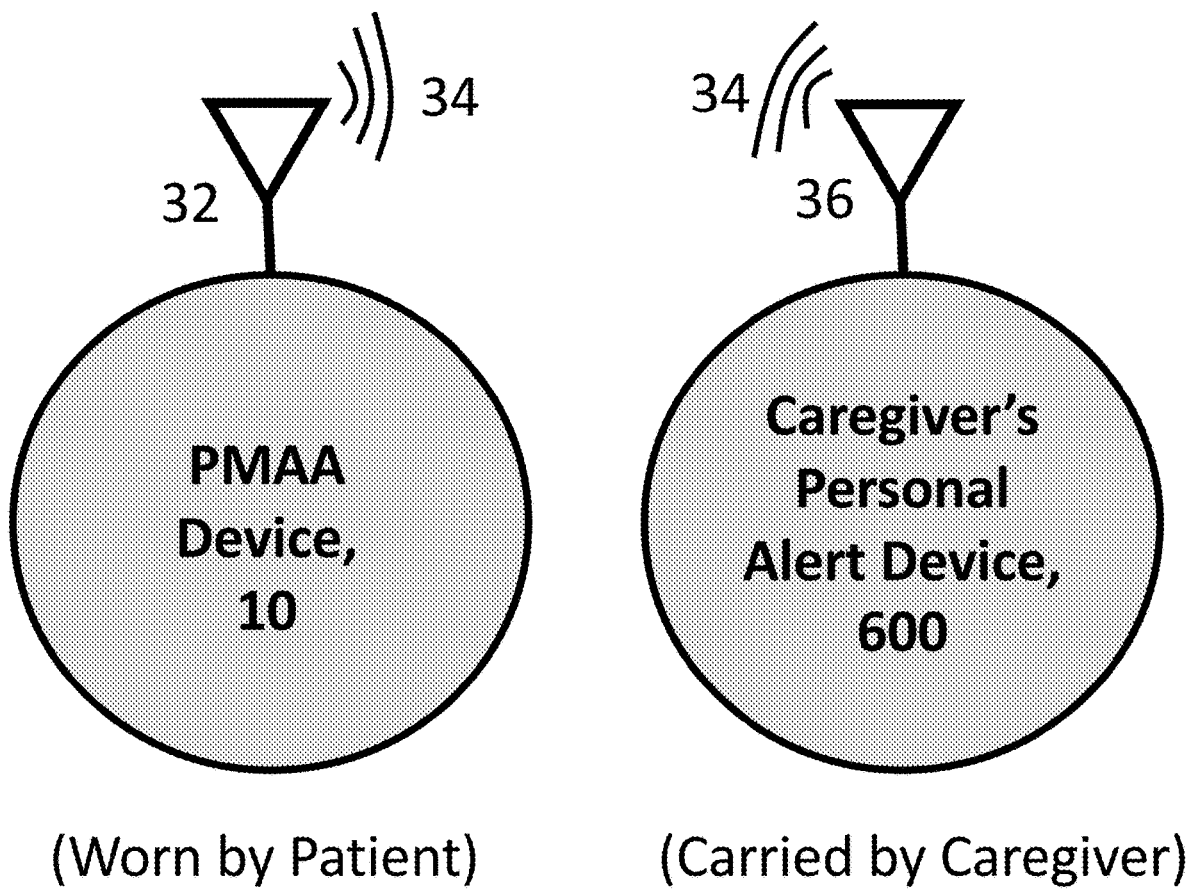
FIG. 2 shows a schematic diagram of an example of a Patient Monitoring and Activity Alert (PMAA) device that communicates with a Caregiver's Personal Alert Device (CPAD) via wireless protocols, according to the present disclosure.

FIG. 2 shows a schematic diagram of an example of a Patient Monitoring and Activity Alert (PMAA) device 10 that communicates wirelessly with a Caregiver's Personal Alert Device (CPAD) 600 via wireless protocols, according to the present disclosure. PMAA device 10 comprises a first antenna 32 located on (or inside) of PMAA device 10 that transmits one or more digital messages 34 via Bluetooth™ protocols to a second antenna 36 located on (or inside) of the CPAD 600.

Figure 3A:
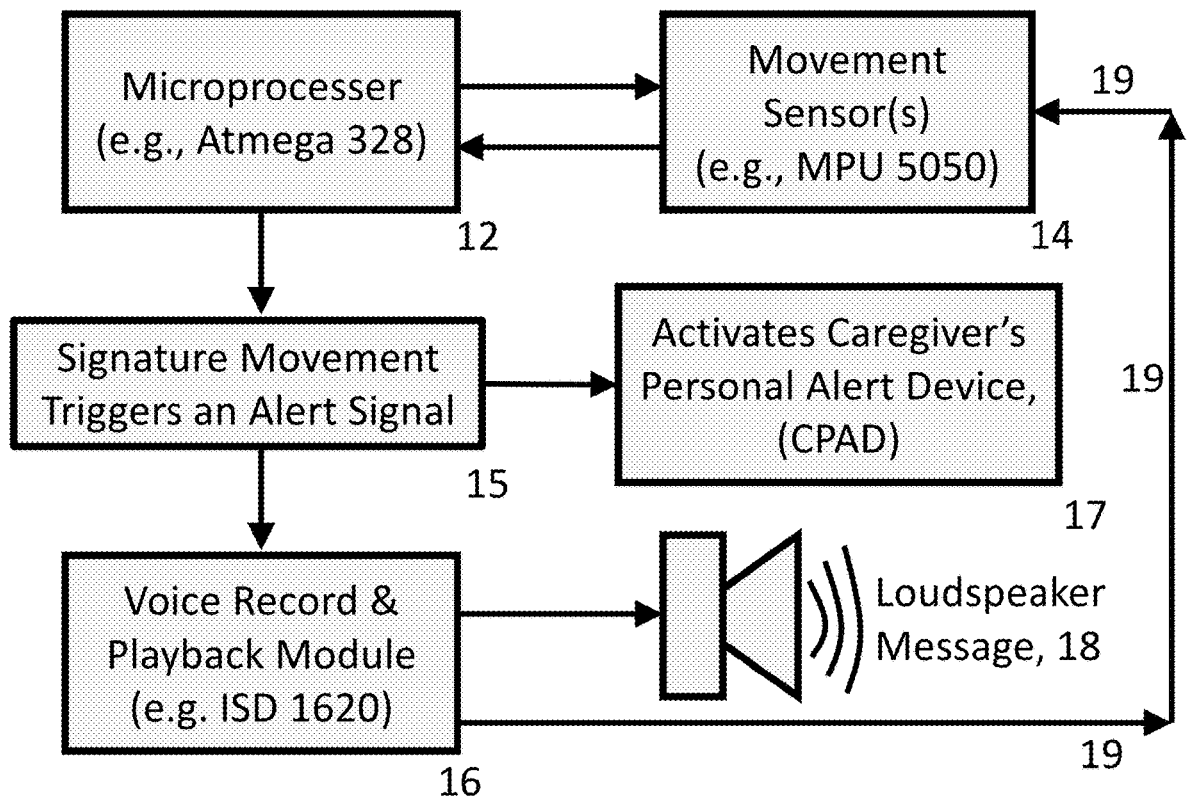
FIG. 3A shows a schematic diagram illustrating of an example of the components of a Patient Monitoring and Activity Alert (PMAA) system 8, according to the present disclosure.

FIG. 3A shows a schematic diagram illustrating of an example of the main components of a Patient Monitoring and Activity Alert (PMAA) system 8, according to the present disclosure. A PMAA device 10 (not shown) is preferably attached by a suitable, removable means of attachment (e.g., a pin) to the patient's clothing upon or near the patients' shoulder, and preferably on the upper back close to a functional ear. When the power is turned ON, microprocessor 12 preferably initiates serial communication with movement sensor(s) 14 and begins a brief calibration sequence when the patient is in a stable upright position to provide "offset factors". To reliably detect the commencement of rising movement, two separate bodily movements can be monitored: (1) a change in attitude/rotation (i.e., change in a rotation angle of the chest from an upright position, See FIG. 1B) and (2) an upward (vertical) motion as the patient stands up (See FIG. 1C). Since these two different sets of data may not be available simultaneously from the sensor(s) 14, some short-term storage, retrieval, and comparison of the data are preferably performed by microprocessor 12 to assure a correct decision is made to trigger and initiate an audible warning message. When the microprocessor's program has made a determination in step 15 that the patient is intending to stand up, it triggers the alert signaling and preferably executes a time delay line allowing the stored audio message to run its full course unimpeded. The audio message (previously recorded by a relative, a close friend, or even the patient himself) is preferably no longer than a full length of the time delay line, (e.g., 12 seconds). Both message selection and audio volume are preferably controlled by the device's microprocessor 12 and audio amplifier 16. Microphone 16 is used for recording the warning message(s) and it may also be used to (1) sample ambient room conditions in order to control the playback volume and/or (2) provide audio frequency equalization, if needed.

Referring still to FIG. 3A, an example of a method of using the PMAA system 8 can comprise the following steps, in the order as presented below:

1. Microcontroller 12 initially calibrates sensor(s) 14;
2. Sensor(s) 14 monitor bodily attitude, orientation, and upward movement;
3. Microprocessor 12 compares sensor data 14 with one or more internal movement models;
4. If a "signature movement event" occurs, then trigger sending an alert signal 15 from PMAA device 10;
5. If there is a match of the signature movement event with the internal movement model(s), then PMAA device 10 announces an audible warning message 16, 18 alerting the patient;
6. Simultaneously with step #5, PMAA device 10 sends an alert signal to the Caregiver's Personal Alert Device (CAPD) 17 of the start of a signature movement event; and
7. If not a match, then continue monitoring bodily movements 14 and repeat steps #1 though #6 in step 19.

Note: the term "signature movement event" in step #4 refers to both: (1) the initial forward rotation of the chest that orients the patient's center of gravity over their feet (see FIG. 1B), followed by (2) an initial upward movement of the entire body as the patient begins to stand up (see FIG. 1C).

Figure 3B:
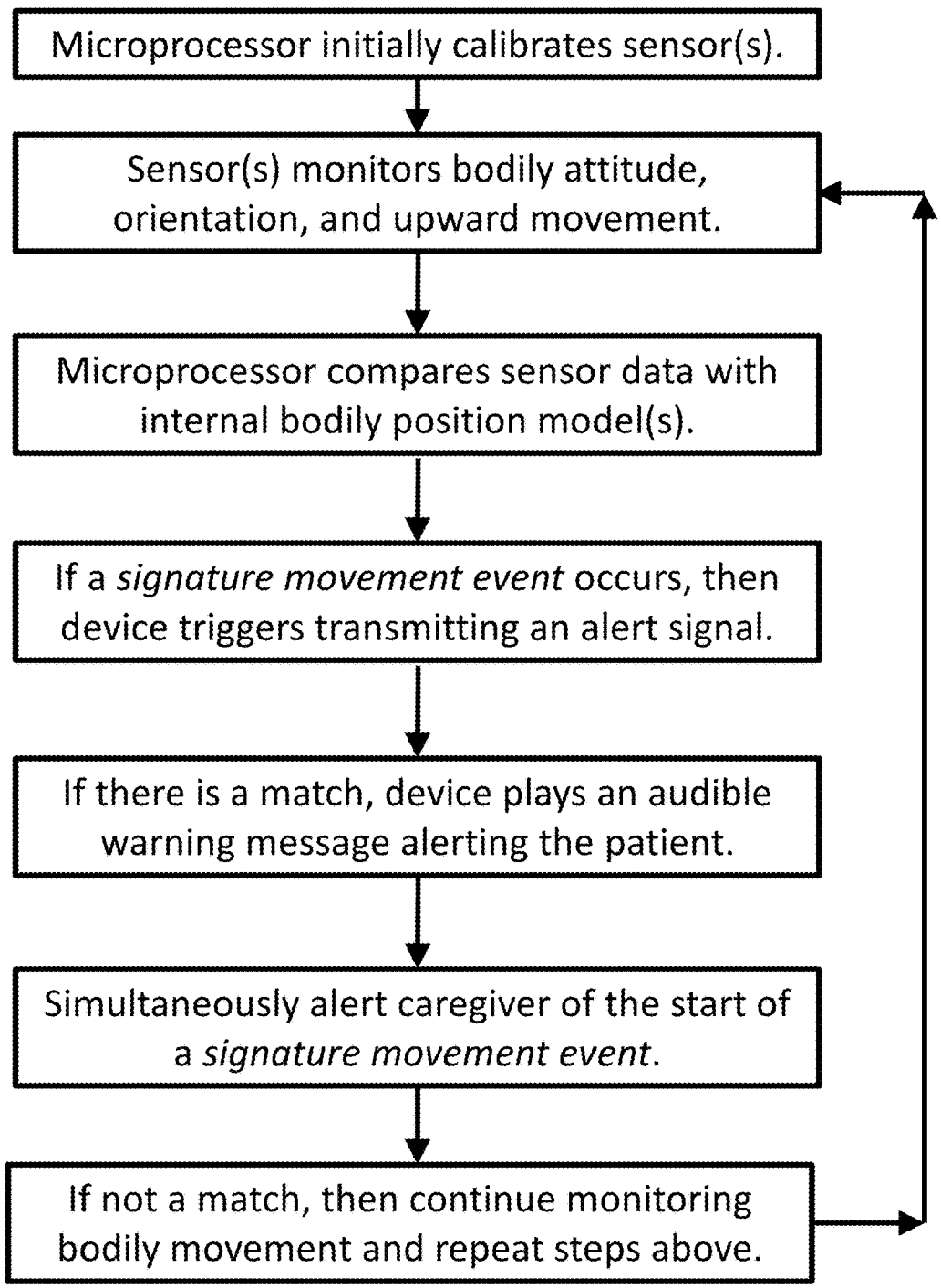
FIG. 3B shows flow chart illustrating an example of a method of using a PMAA system 8, according to the present disclosure.

FIG. 3B shows flow chart illustrating an example of a method of using a PMAA system 8, according to the present disclosure. This flow chart refers back to FIG. 3A, and the method steps listed immediately above.

Some preferred characteristics of a PMAA system 8 can include the following desirable qualities, including combinations and sub-combinations thereof:
- Inconspicuous and compact design to prevent patient's annoyance and removal;
- Easily attachable/removable by unskilled personnel;
- Tolerant of inaccurate placement;
- Loud enough to command the patient's full attention;
- Able to accurately predict the initial body movements of a patient that indicates an intent to stand up;
- Easily recordable by unskilled users;
- Able to faithfully reproduce a voice from the audio recorder; and
- Is compatible with institutional practice.

A PMAA device 10 may be embedded in worn items of clothing, such as: a hat, eyeglasses, hearing aid, shirt collar, jewelry, necklace, earrings, and/or combinations thereof. Alternative systems to a compact, standalone electronic device may be used, such as a computer application on a mobile smart phone or other wearable device such as a smart watch, smart fitness monitor, smart eyeglasses, and/or a smart Virtual Reality Headset. However, in those cases, the message needs to be preferably loud enough for the patient to hear in case the device is not located close by to the patient's ear when the patient starts to move and stand up.

Figure 4:
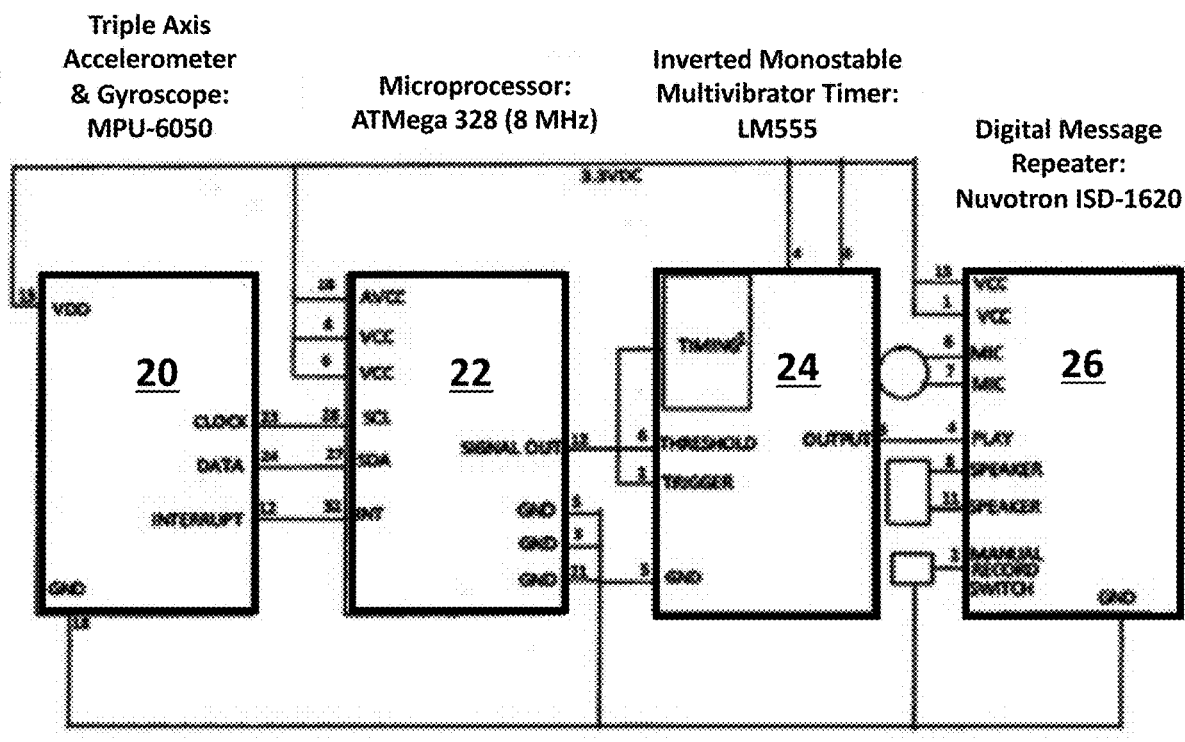
FIG. 4 shows a schematic circuit diagram of another example of a Patient Monitoring and Activity Alert (PMAA) device, according to the present disclosure.

FIG. 4 shows a schematic circuit diagram of another example of a Patient Monitoring and Activity Alert (PMAA) device, according to the present disclosure. An inertial motion unit sensor 20 (e.g., Invesense MPU-6050), which includes a MEMS 3D accelerometer and a MEMS 3D gyroscope integrated chip with an integrated digital motion processor, can be used to continuously provide the 3D coordinates of the device's position and spatial orientation, perform preliminary analysis and filtering, and store the data in a FIFO register. At start up, microprocessor 22 (e.g., Atmega 328 3.7 V/8 MHz Arduino Mini-Pro) initiates communication protocols and calibrate the sensor(s) data. Initially, microprocessor 22 pauses briefly for the initial body position data to settle down, and then the readings are recorded and analyzed as a baseline for use in future computations (i.e., to create "offset factors"). Microprocessor 22 then continuously monitors and examines incoming sensor 20 data to find correspondence with one or more programmed motion models (which have been derived from numerous trials). Timing module 24 (e.g., LM-555) and Digital Message Repeater 26 (e.g., Nuvotron ISD-1620) are also shown in FIG. 4, and are all operably connected to a power supply (not shown), which can be a battery with 3.3 V to 3.7 V. Timing module 26 can be an Inverted Monostable Multivibrator Timer module or chip.

Figure 5:
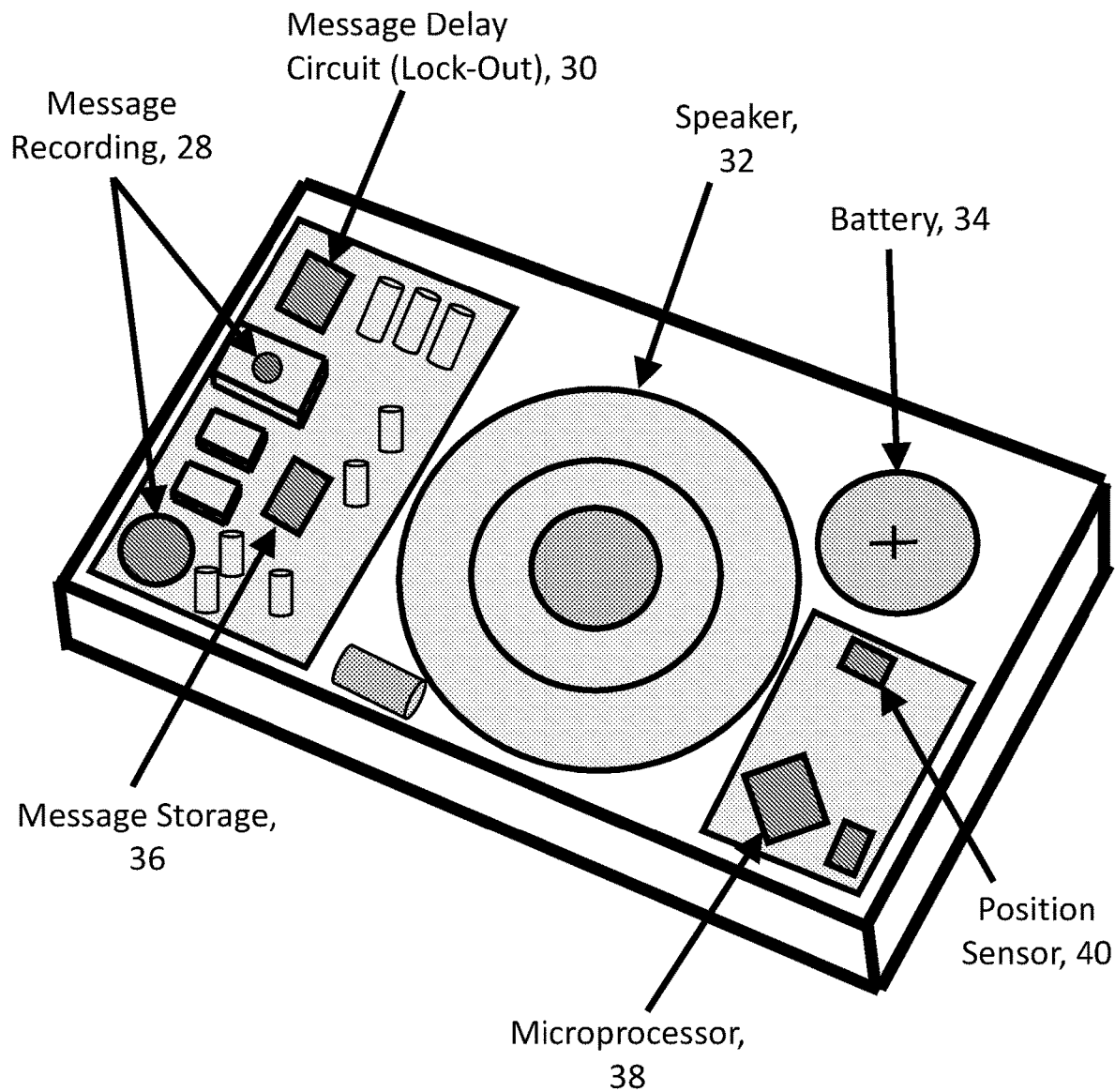
FIG. 5 shows a photograph of an early prototype electronic Patient Monitoring and Activity Alert (PMAA) device, according to the present disclosure.

FIG. 5 shows a photograph of a prototype electronic Patient Monitoring and Activity Alert (PMAA) device 10, according to the present disclosure, that was constructed and successfully tested. At the first stage of monitoring and predicting (of the patient rising from a sitting position) the position sensor(s) 40 detect the body's forward rotation of the chest, and subsequent shift of weight over the patient's feet. The second stage is the initiation of upward movement by the patient, which is also monitored by sensor(s) 40. At an optimum predictive moment (i.e., when a verbal warning is most effective in halting the desire to stand up), a "lock out" circuit (third stage) comprising, for example, a Message Delay Circuit IC 555 (one shot circuit 30) is initiated to isolate the message being announced from interrupting signals inside of the microprocessor 38. The device's timing corresponds to a length of each message. The last stage is communicating with the patient 6. An audio recording section (message recording 28, message storage 36, and loudspeaker 32) comprising a multiple message storage block and an audio amplifier (not identified), comprising, for example, a Nuovoton ISO1620 voice recorder 16 (with associated passive components), that drives a small (e.g., 2 inch diameter) monaural PUI AS05008 PR-A-R 1W 8-Ohm 84 OBA loudspeaker 32. The prototype PMAA device 10 is powered by, for example, a generic 3.7V, 800 mAh cell phone battery 34. The dimensions of device 10 can be approximately 2.5×4.5×0.5 inches, for example.

Figure 6:
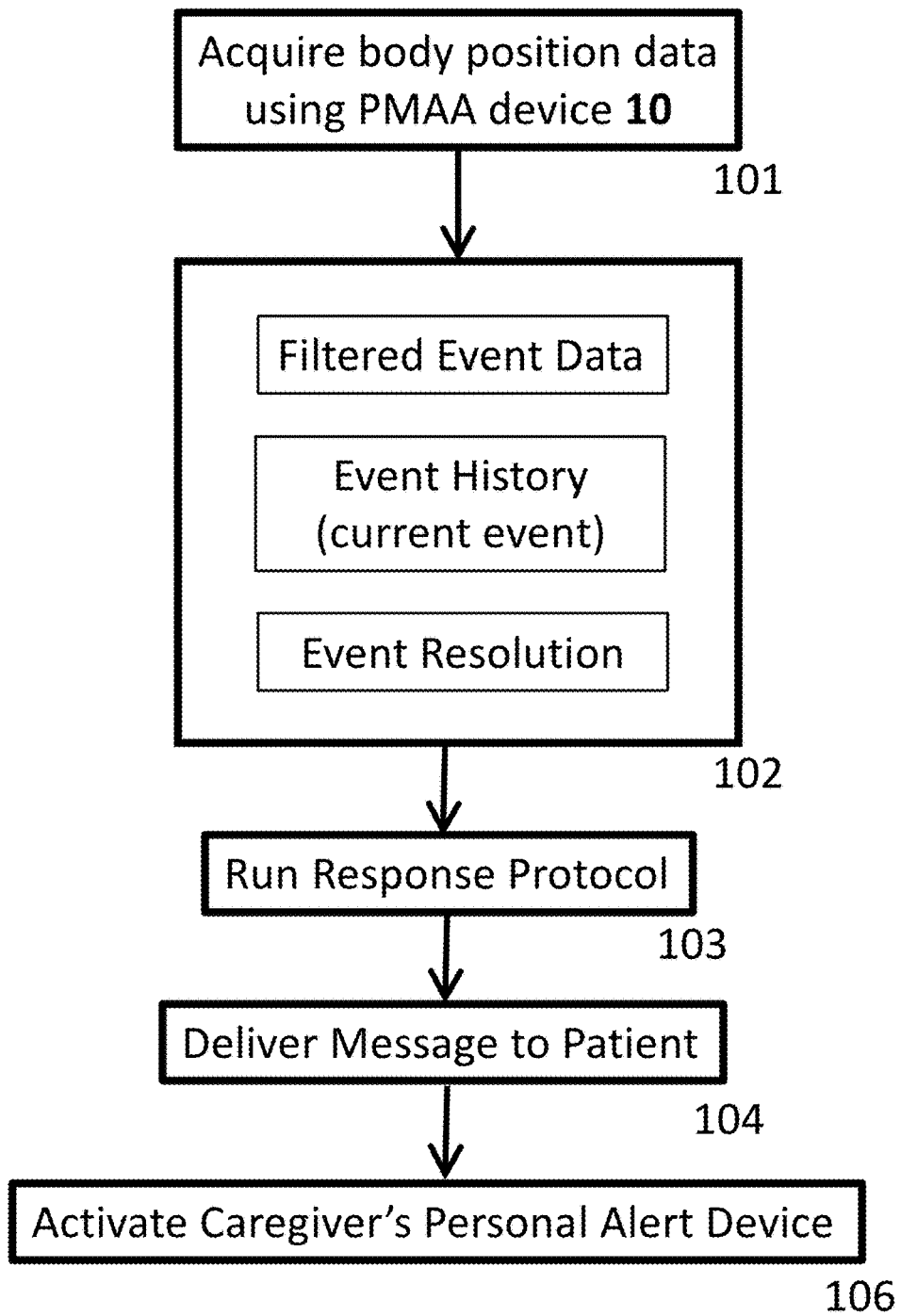
FIG. 6 shows a simplified flow chart illustrating an example of system operating steps, according to the present disclosure.

FIG. 6 shows a simplified flow chart illustrating an example of an PMAA device according to the present disclosure. In step 101, a PMAA device 10 is provided comprising a wearable patient monitoring device 10 that has minimal size, weight, and power consumption. Device 10 may comprise one or more surface-mounted integrated chips (IC's), which can include: a 3D accelerometer, a 3D gyroscope, a 3D magnetometer, an atmospheric pressure sensor, a temperature gauge, and/or combinations thereof, whose information may yield data predictive of a patient's intent to stand up. However, emphasis, in a preferred embodiment at least, favors monitoring the least amount of data necessary to successfully determine an indicative (predictive) movement that leads to an intent to rise from a seated or prone position. The Run Response Protocol Step 103 and the Deliver Message to Patient step 104 are natural outcomes of this effort, and they will be fully explained in subsequent paragraphs.

Figure 7:
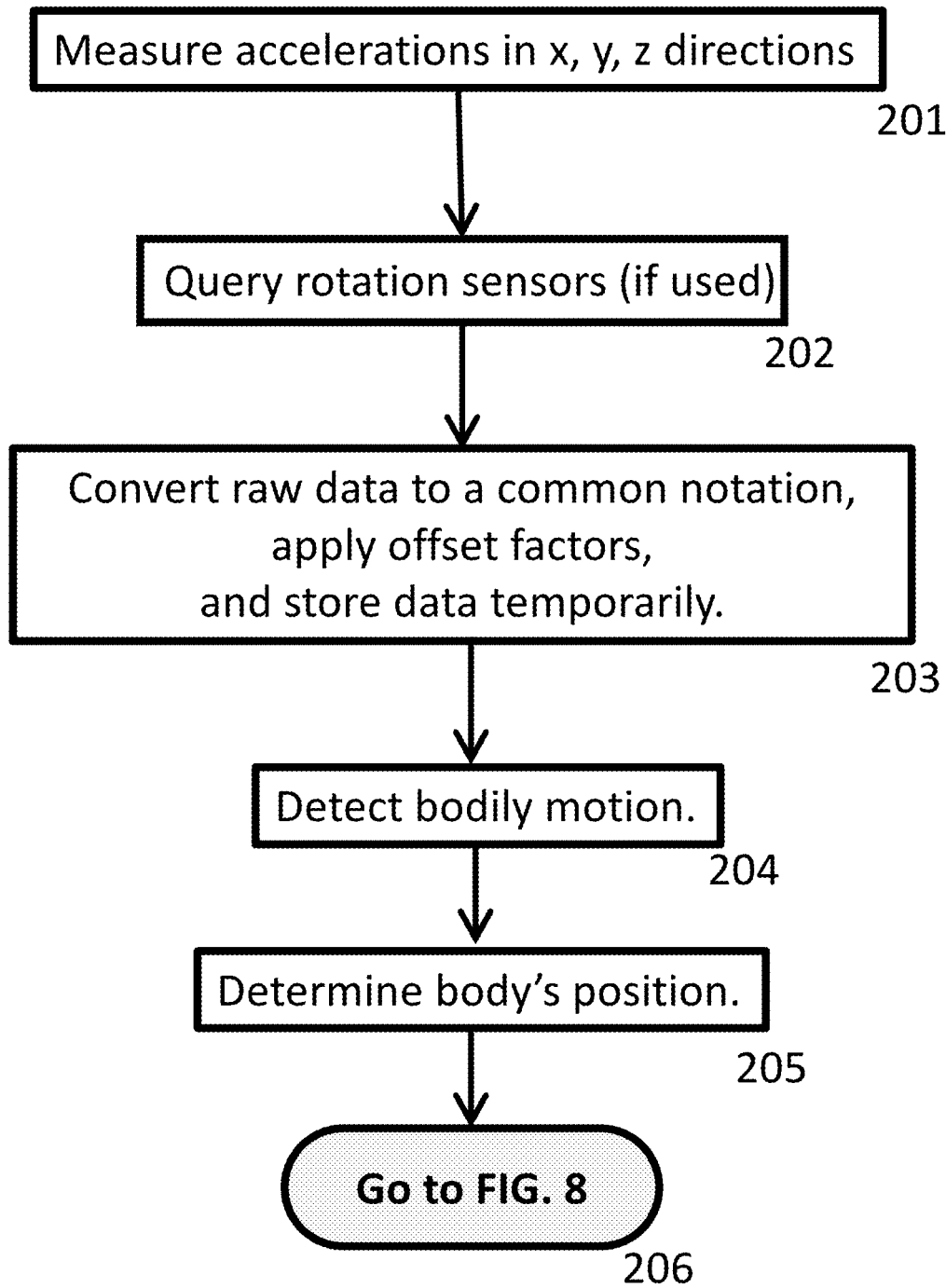
FIG. 7 shows a flow chart illustrating an example of a method of examining and processing Measured Movement Data, according to the present disclosure.

FIG. 7 shows a more detailed description of an example of a flow chart illustrating a Data Collection protocol, according to the present disclosure. Steps 201 and 202 show data accumulation and subsequent processing to ensure compatibility (in step 203).

Figure 8:
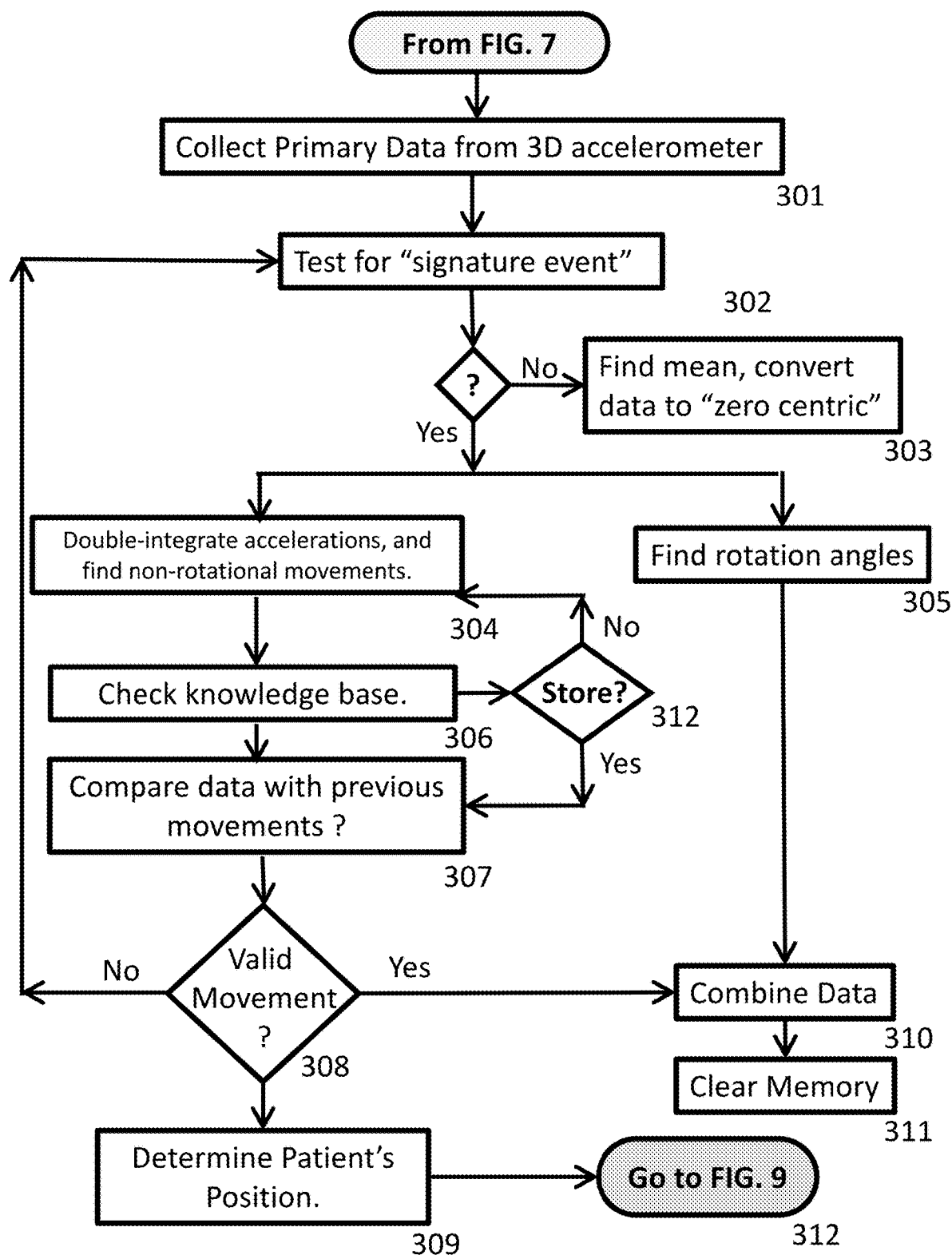
FIG. 8 shows a continuation of the flow chart previously shown in FIG. 7, illustrating an example of a Response Protocol method, according to the present disclosure.

FIG. 8 shows a continuation of the flow chart previously shown in FIG. 7, illustrating an example of a method of Examining and Processing Data, according to the present disclosure. In step 301 (measuring sensor data from the 3D accelerometer), the measured accelerometer data tends to float with no firm reference to a zero median. Calculations to determine non-angular (i.e., vertical) patient motion depend on having a firm reference position. Step 302 tests for a low-activity period, and the measured sensor data is set equal to zero. In step 303, this is corrected by constantly monitoring the rest state (low event state) for an average departure from the zero reference and then applying a corrective signal which, in effect, creates a second (modified) data set that is used in further calculations. 3D rotational angles in step 305 can be derived (integrated?) from the measured 3D accelerometer data, which indicates the change from a body's vertical orientation to one in which much of the body's mass has rotated forward and centered itself over the patient's feet before standing up. Alternatively, a 3D gyroscope sensor can be used to directly measure the rate of 3D rotation angles (which requires time integration). In step 304, a process of double-integration reveals positive movement of the monitoring device in one of the six movement directions, as allowed by the sensor's design. Depending on the magnitude and direction of the patient's motion, when compared to a history (i.e., a first knowledge base) of their motions (steps 306 and 307), then appropriate decisions may be made that allow either: (1) storage of the position sensor's result to compare with a subsequent reading of a caregiver's verbal reinforcement, or (2) an acceptance of the movement as a valid movement event. Combining the measured movement event data in steps 309 and 310 results in magnitude, direction, and rotational angles in all three directions: x, y, and z. Reading a second knowledge base in step 310 resolves this positioning data into, for example, five different patient models that define his/her implied activity (e.g., preparing to stand).

Figure 9:
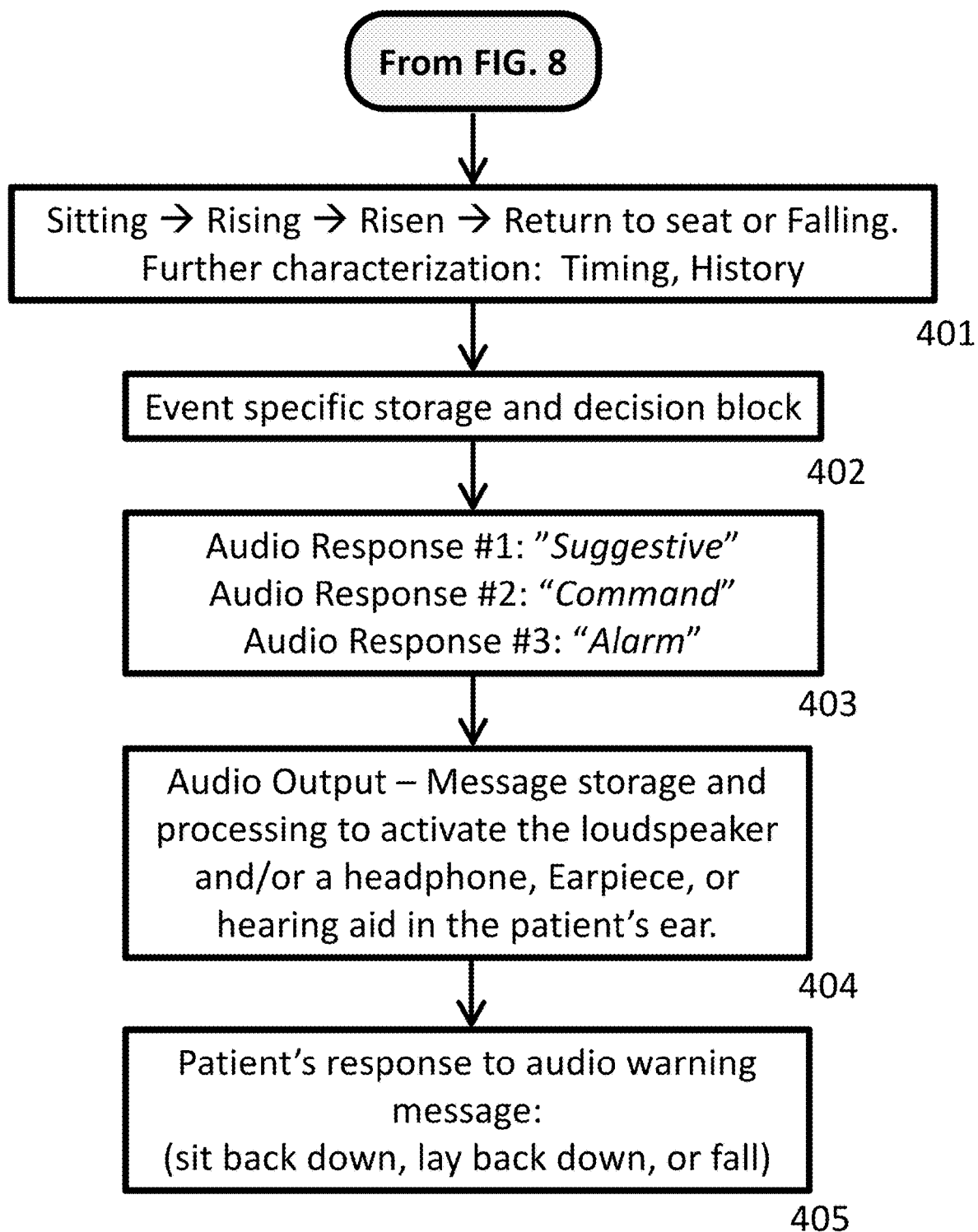
FIG. 9 shows a flow chart continuation from FIG. 8, illustrating an example of a method of Recording and Playing Back of message(s) using a Patient Monitoring and Activity Alert (PMAA) device, according to the present disclosure.

FIG. 9 shows a continuation of the flow chart previously shown in FIG. 8, showing an example of a Response Protocol method, according to the present disclosure. The measured positional information (data) in step 402 is reduced to three possible responses and escalating loudspeaker volume levels in step 403 ("Suggestive", "Command", and "Alarm"). Step 404 indicates that the patient's response to the loudspeaker's audio messaging will be monitored. This, of course, is continually being done by the position sensor's continuous data gathering.

Figure 10:
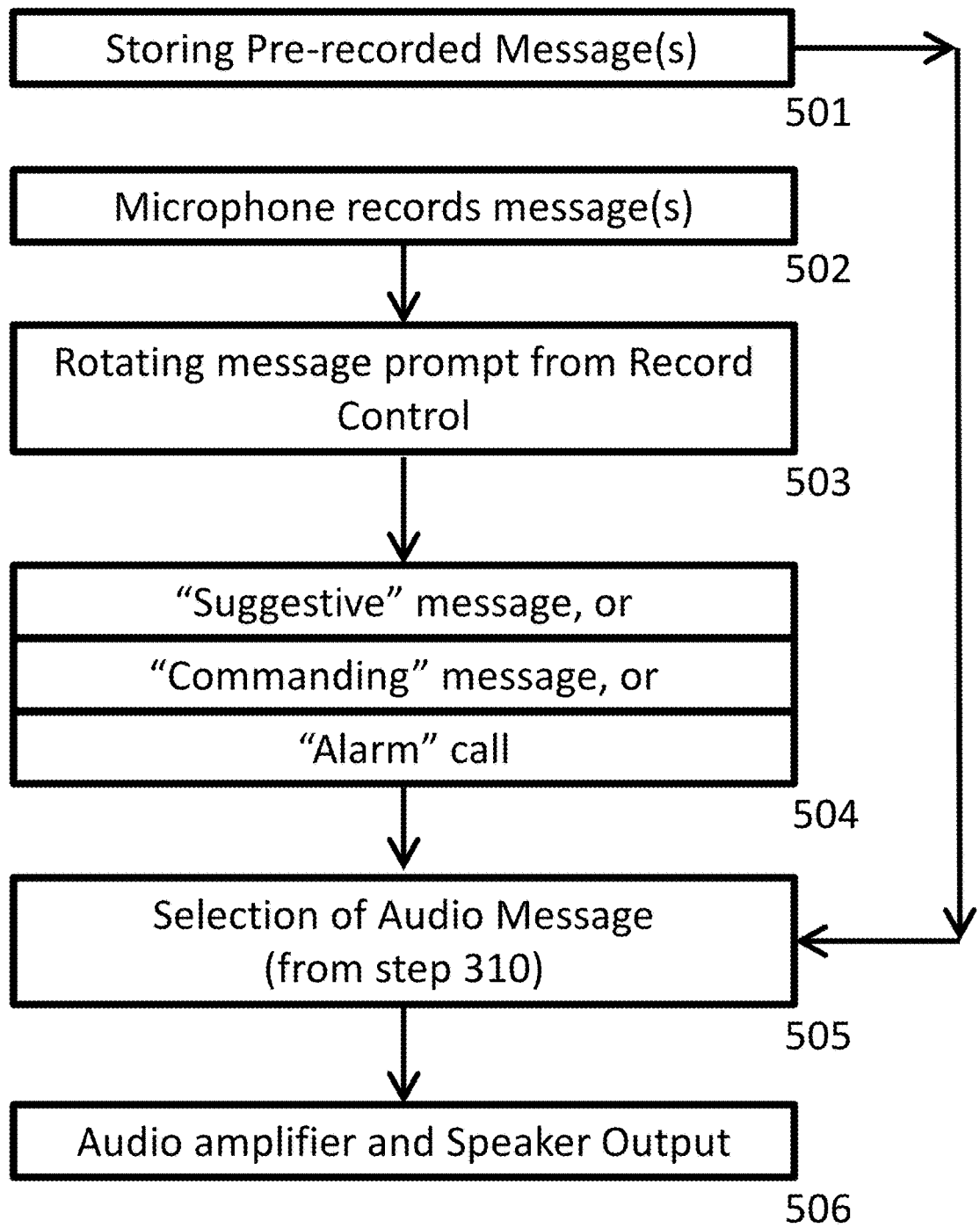
FIG. 10 shows a flow chart illustrating an example of a method of recording and playing back of message(s) using a Patient Monitoring and Activity Alert (PMAA) device, according to the present disclosure.
Figure 11A:
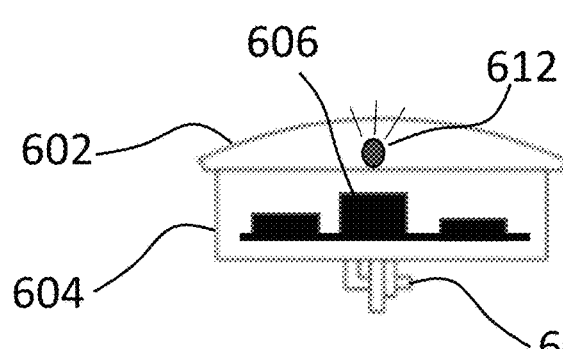
FIG. 11A shows a side view of an example of a Caregiver's Personal Alert Device (CPAD), according to the present disclosure.
Figure 11B:
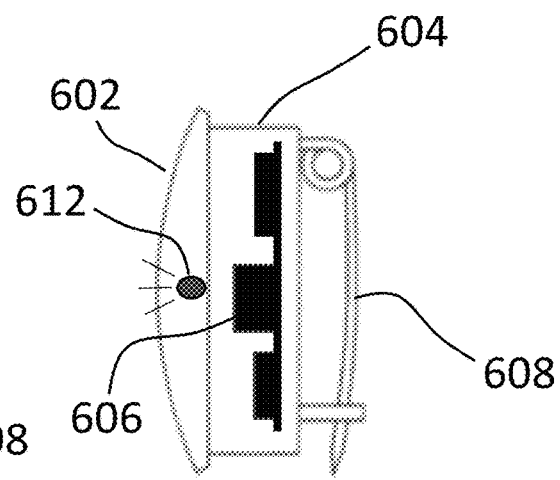
FIG. 11B shows a side view of an example of a Caregiver's Personal Alert Device (CAPD), according to the present disclosure.
Figure 11C:
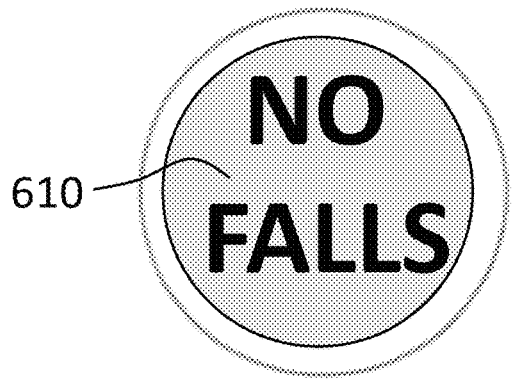
FIG. 11C shows a front view of an example of a Caregiver's Personal Alert Device (CPAD), according to the present disclosure.
Figure 11D:
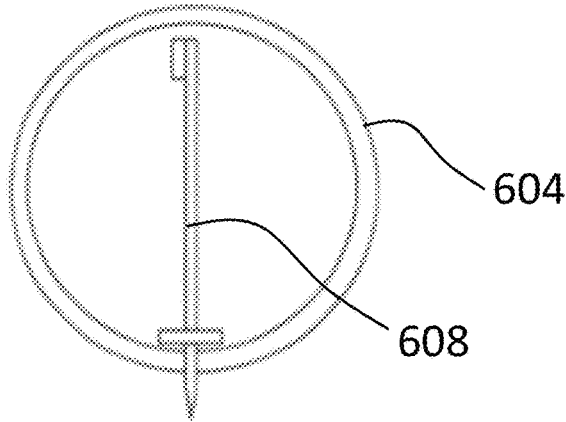
FIG. 11D shows a rear view of an example of a Caregiver's Personal Alert Device (CPAD), according to the present disclosure.
Figure 12:
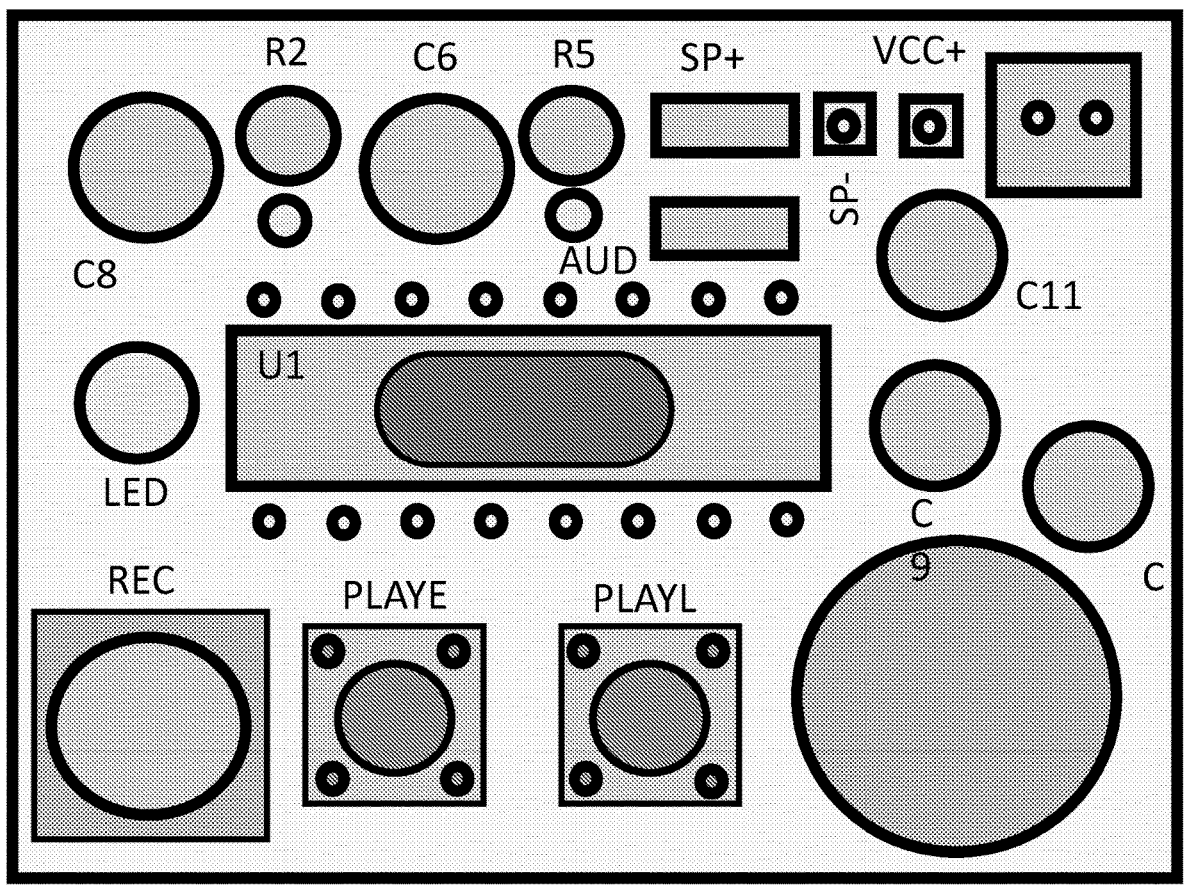
FIG. 12 shows a photograph of an example of an audio recording and playback module (e.g., NC-ISD-1620B), according to the present disclosure.

FIG. 10 shows an example of a flow chart illustrating a method of Recording and Playback of Message(s) using a patient monitoring system 8, according to the present disclosure. Flash memory 502 is filled with prerecorded messages suggestive of the style preferably recorded by family members or friends most likely to have some influence over the patient. Recording means 502 and 503 may be included in the wearable monitoring device if space allows, or used remotely as a computer application. The examples of message styles listed as step 504 are listed as a minimum of potentially useful messages. Step 505 refers back to FIG. 9, while steps 310 and 506 comprise an electromechanical means for generatic audible reproduction (e.g., loudspeaker output 506).

FIG. 11A, 11B, 11C, and 11D shows four different views of an example of a Caregiver's Personal Alert Device (CPAD) 600, according to the present disclosure. CPAD container 604 comprises internal electronics 606 (including, for example, a microcomputer programmed to control the LED's response rate, a Bluetooth communication module, a Li-ion battery and charger, and a power control switch) contained in a lightweight, compact and transparent plastic case 602 that can be attached with a pin 608 to the caregiver's clothing. A bright LED light 612 can be mounted inside the alert device 600, which provides a fixed or flashing visual alert signal when a patient's signature movement event triggers simultaneous activation of the PMAA device 10 and the CPAD alert device 600. CPAD 600 can also comprise a loudspeaker for announcing a verbal message as an alert signal. Optionally, CPAD 600 can comprise a vibrating member that causes CPAD 600 to vibrate when alerted. Finally, a simple printed message 610, e.g., "NO FALLS", in a large type font can optionally be attached to the front cover 602 of device 600.

The PMAA device 10 can comprise a fabric enclosure that contains all of the electronics, and can be worn about the patient's neck (e.g., as a scarf), which can be attached to cording with a sliding fastener (also known as a "bolo tie"), which can display familiar emblems on a cover of the device to gain acceptance by the patient (e.g., the patent's first name, "My Hero", a military emblem, the National Flag, and/or combinations thereof may be displayed).

Figure 13:
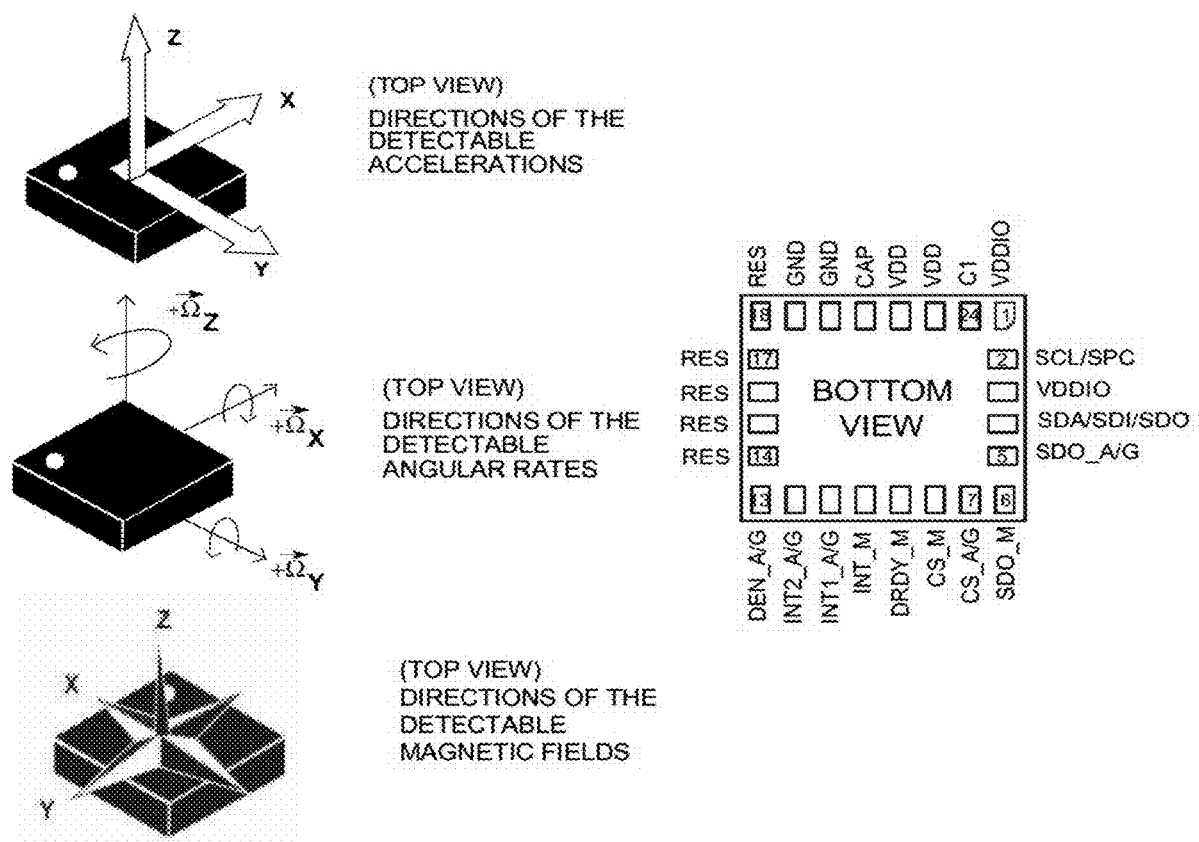
FIG. 13 shows a perspective view of an example of a combined 3D Accelerometer, 3D Gyroscope, and 3D Magnetometer IC (e.g., iNEMO LSM9DS1), according to the present disclosure.

FIG. 13 shows a perspective view of an example of a combined 3D Accelerometer, 3D Gyroscope, and 3D Magnetometer IC (e.g., iNEMO LSM9DS1), according to the present disclosure. Not all of the sensors in this combined IC have to be used at the same time; some are optional.

Figure 14:
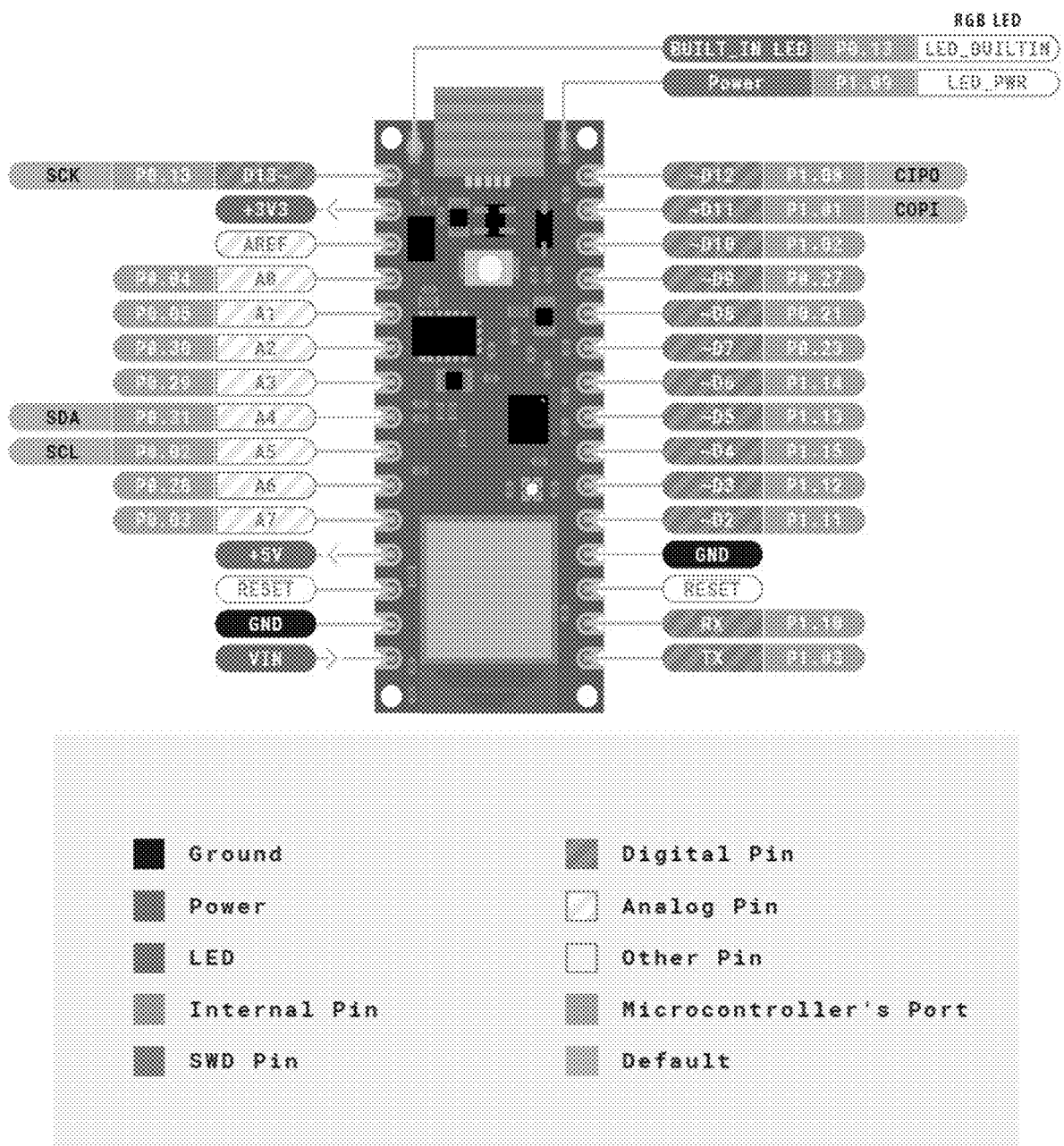
FIG. 14 shows a top view of an example of a microprocessor IC (e.g., Arduino NANO 33 BLE), according to the present disclosure.

FIG. 14 shows a top view of an example of a microprocessor IC pin diagram (e.g., Arduino NANO 33 BLE), according to the present disclosure.

Figure 15:
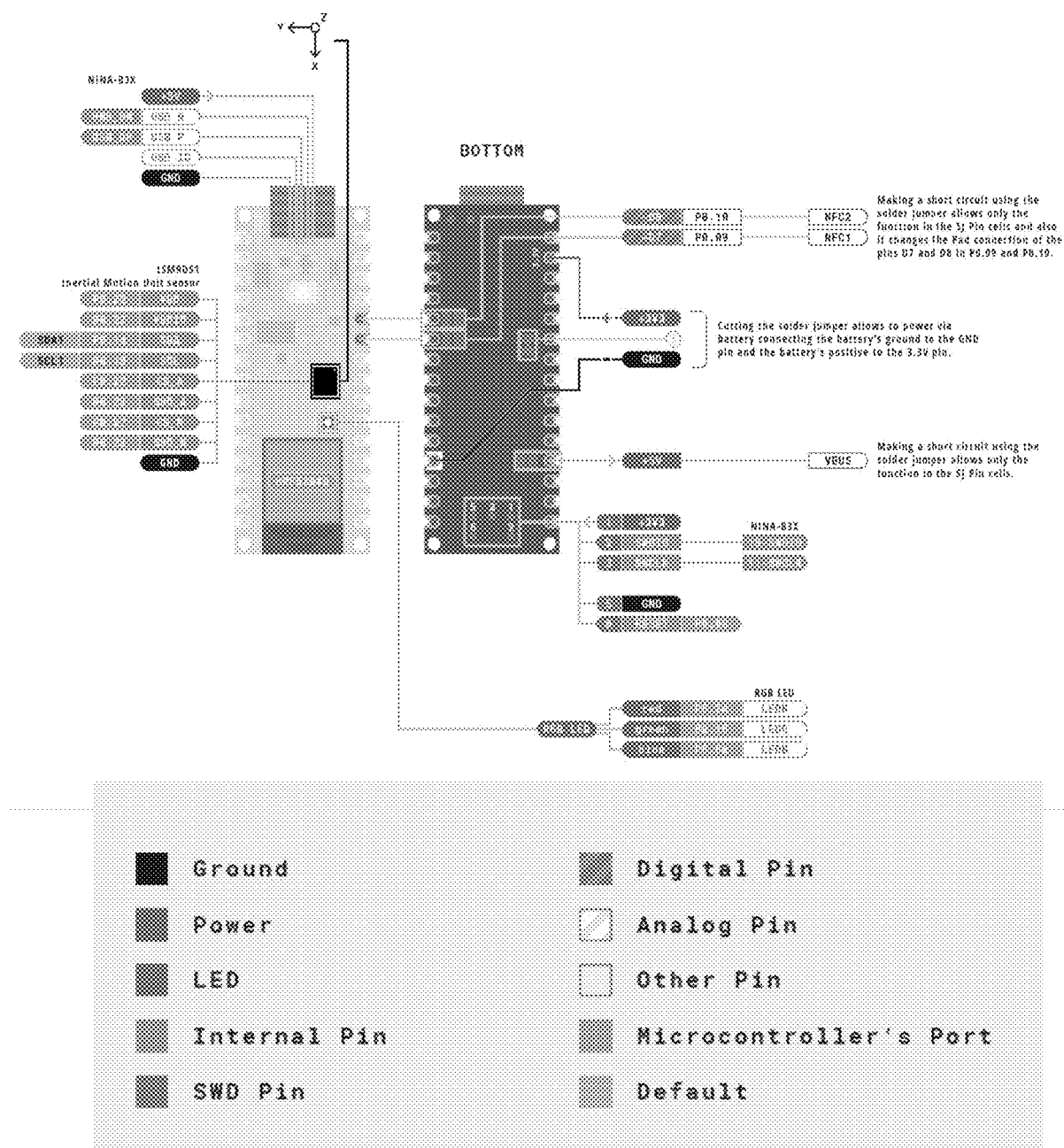
FIG. 15 shows a bottom view of an example of a microprocessor IC (e.g., Arduino NANO 33 BLE), according to the present disclosure.

FIG. 15 shows a bottom view of an example of a microprocessor IC pin diagram (e.g., Arduino NANO 33 BLE), according to the present disclosure.

Figure 16:
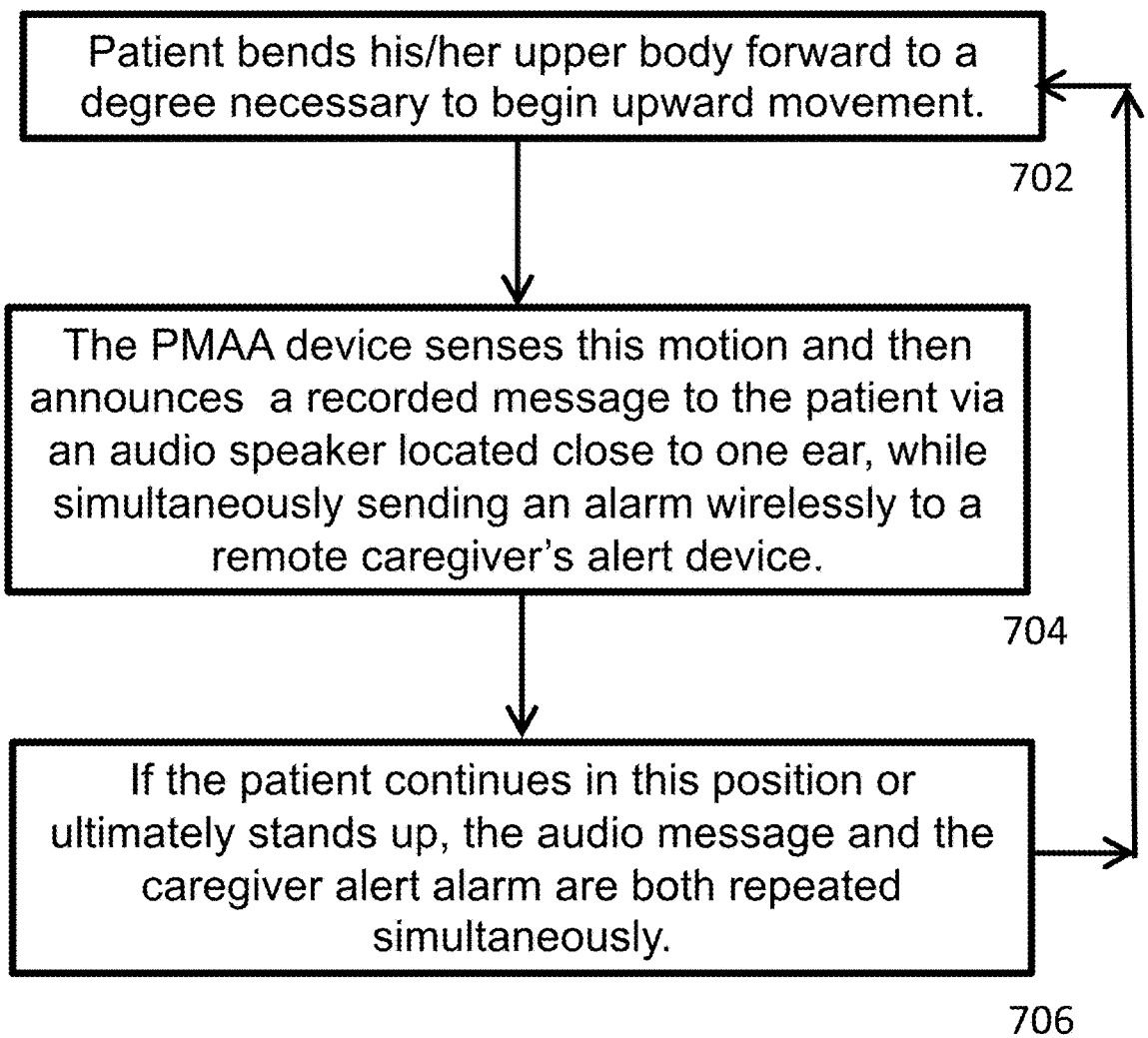
FIG. 16 shows a flow chart illustrating an example of a method of using a PMAA System, according to the present disclosure.

FIG. 16 shows a flow chart illustrating an example of a method of using a PMAA System 8, according to the present disclosure. The method can comprise three steps, performed in the order as listed below:
  Step 702: Patient rotates his/her upper body forward to a degree necessary to begin upward movement and then begins to stand up.
  Step 704: The PMAA device senses this "signature" motion and then announces a recorded "suggestion" to the patient via an audio speaker located close to one ear, and also sends a simultaneous alarm wirelessly to a remote caregiver's personal alert device (CPAD).
  Step 706: If the patient continues in this position or ultimately stands up, the audio message and the caregiver alert alarm are both repeated simultaneously.

Figure 17:
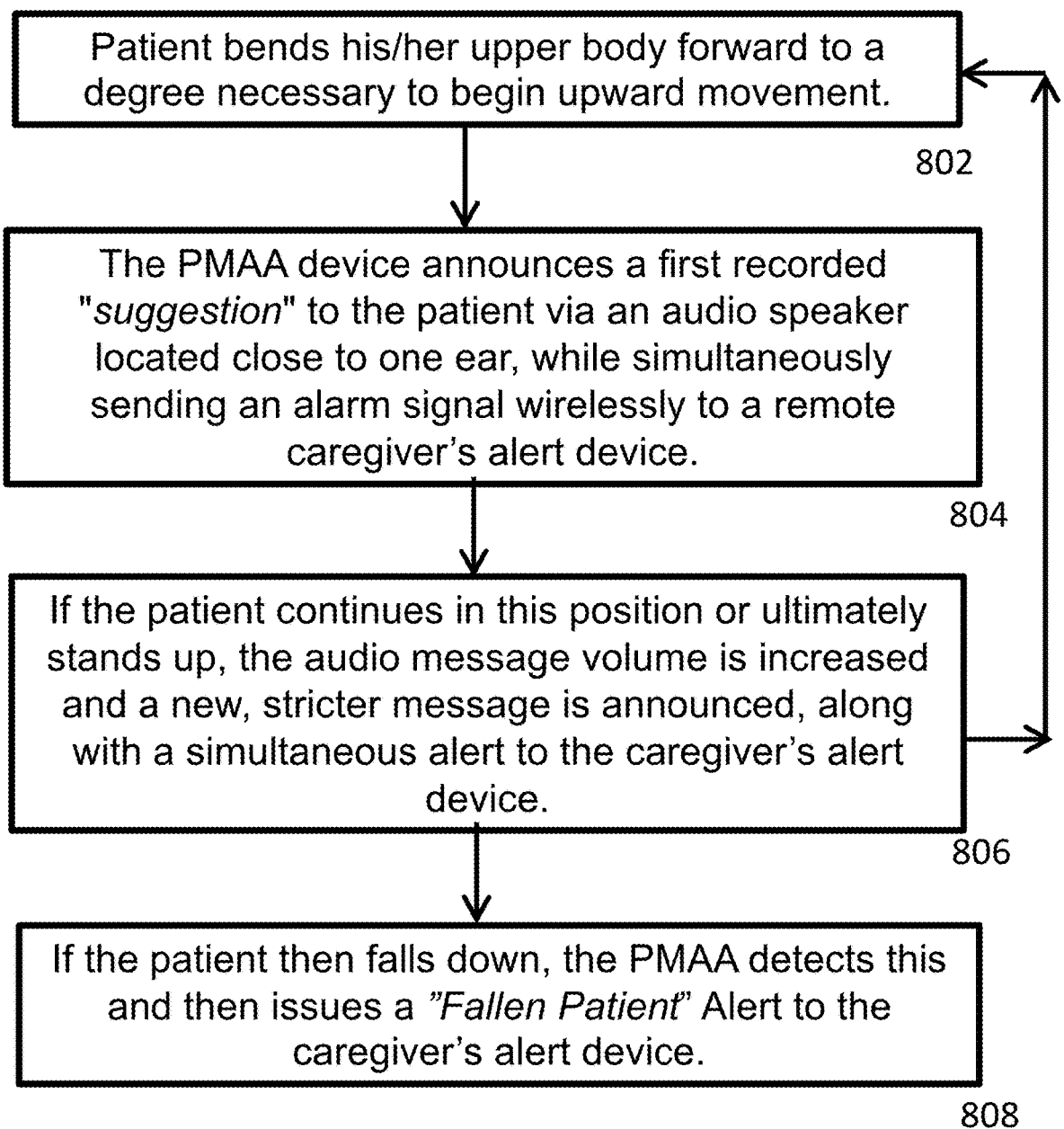
FIG. 17 shows a flow chart illustrating an example of another method of using a PMAA System, according to the present disclosure.

FIG. 17 shows a flow chart illustrating another example of a method of using a PMAA System 8, according to the present disclosure. The alternate method can comprise four steps, performed in the order as listed below:
  Step 802: Patient rotates his/her upper body forward to a degree necessary to begin upward movement and then begins to stand up.
  Step 804: The PMAA device 10 senses this "signature" motion and then announces a recorded "suggestion" to the patient via an audio speaker located close to one ear, and also simultaneously sends an alarm signal wirelessly to a remote caregiver's personal alert device (CPAD).
  Step 806: If the patient continues in this position or ultimately stands up, the audio message volume is increased and a new, stricter message is announced, along with a simultaneous alert to the caregiver's alert device.
  Step 808: If the patient then falls down, the PMAA device 10 can detect this and then issues a "Fallen Patient" Alert to the caregiver's personal alert device (CAPD).

PMAA device 10 and/or CPAD 600 can include a vibrator element located inside of each device, that causes the devices to vibrate each time an alert is triggered, transmitted, and/or received.

An example of a method of discouraging a disabled person from falling can comprise the following steps, performed in the order presented:
  (1) attaching an electronic Position Monitoring and Activity Alert (PMAA) device to a patient;
  (2) monitoring and detecting changes in the patient's bodily orientation that are predictive of a patient's intent to stand up;
  (3) using a microprocessor to compare monitored changes in the patient's bodily orientation to one or more internal positioning model(s) that are programmed inside of the microprocessor;
  (4) announcing, with the PMAA device, a verbal warning message to the patient when the monitored changes match the one or more internal positioning model(s); and then telling, with the PMAA device, the patient to "not stand up" and/or to "sit (or lie) back down"; and
  (5) simultaneously along with step (4), transmitting one or more caregiver alert signals to a Caregiver's Personal Alarm Device (CPAD), thereby alerting the caregiver that the patient is starting to stand up; and then
  (6) the caregiver subsequently intervenes with the patient to discourage the patient from standing up and possibly falling down.

Alternatively, another example of a method of discouraging a disabled person from falling can comprise performing the following steps, performed in the order as presented:
  (1) attaching a Position Monitoring and Activity Alert (PMAA) device to a patient, who is sitting down, or lying in a prone position;
  (2) providing a caregiver with a Caregiver's Personal Alarm Device (CPAD);
  (3) defining a "signature movement event" as comprising predictive bodily movements that comprise two motions: (a) a forward rotation of a patient's upper body that positions the patient's center of gravity over his/her feet, and (b) a vertical movement of the patient's entire body when starting to stand up;
  (4) detecting the "signature movement event" from step (3) by using one or more motion detecting sensors located inside the PMAA device to compare the sensor data to one or more internal model(s) of patient movement kinematics;
  (5) playing a recorded warning message to the patient, which instructs the patient to "stop standing up" and/or to "sit (or lie) back down"; and
  (6) simultaneously, along with step (5), sending an alert signal to a Caregiver's Personal Alert Device (CPAD) that alerts the caregiver of the patient's intent to stand up;
  wherein the alert signal is sent when a signature movement event is detected in step (4).

PMAA device 10 can optionally include a GPS chip (Global Positioning Satellite), for giving a precise location of the PMAA device 10 (and, hence, the patient's global position location). Optionally, a method of using PMAA device 10 can comprise sending an alert signal to CPAD 600, without simultaneously giving a verbal warning message to the patient (i.e., generating a "silent alarm" to the caregiver).

Motion sensors with remote alarms allow caregivers to focus on their responsibilities, while maintaining their peace of mind. The combined PMAA device and CPAD device are useful pieces of equipment that can assist caregivers and prevent burnout. When providing palliative care to elders, most caregivers struggle to get a good night's sleep. However, with the inclusion of motion sensor alarms for the elderly, they will no longer have to check on the resident every five minutes, while also being able to provide 24/7 support and care.

Many different embodiments have been disclosed herein, in connection with the above description and the Drawings. It will be understood that it would be unduly repetitious and obfuscating to literally describe and illustrate every combination and sub-combination of these embodiments. Accordingly, all embodiments can be combined in any way and/or combination, and the present specification, including the drawings, shall be construed to constitute a complete written description of all combinations and sub-combinations of the embodiments described herein, and of the manner and process of making and using them, and shall support claims to any such combination or sub-combination.

The foregoing is provided for purposes of illustrating, explaining, and describing embodiments of the present disclosure. Modifications and adaptations to these embodiments will be apparent to those skilled in the art and may be made without departing from the scope or spirit of the present disclosure.

As used herein and in the appended claims, the singular forms "a", "an", and "the" include plural referents unless the context clearly dictates otherwise.

It should be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein, unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

In many instances entities are described herein as being coupled to other entities. It should be understood that the terms "coupled" and "connected" (or any of their forms) are used interchangeably herein and, in both cases, are generic to the direct coupling of two entities (without any non-negligible (e.g., parasitic) intervening entities) and the indirect coupling of two entities (with one or more non-negligible intervening entities). Where entities are shown as being directly coupled together or described as coupled together without description of any intervening entity, it should be understood that those entities can be indirectly coupled together as well, unless the context clearly dictates otherwise.

While the embodiments are susceptible to various modifications and alternative forms, specific examples thereof have been shown in the drawings and are herein described in detail. It should be understood, however, that these embodiments are not to be limited to the particular disclosed form, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

An equivalent substitution of two or more elements can be made for any one of the elements in the claims below, or that a single element can be substituted for two or more elements in a claim. Although elements can be described above as acting in certain combinations and even initially claimed as such, it is to be expressly understood that one or more elements from a claimed combination can in some cases be excised from the combination and that the claimed combination can be directed to a sub-combination or variation of a sub-combination.

It will be appreciated by persons skilled in the art that the present embodiment is not limited to what has been particularly shown and described herein. A variety of modifications and variations are possible, in light of the above teachings without departing from the following Claims.

What is claimed is:

1. A method of discouraging a disabled person from falling, comprising the following steps, performed in the order presented:
   (1) attaching an electronic Position Monitoring and Activity Alert (PMAA) device to a patient;
   (2) monitoring and detecting changes in a patient's bodily orientation that are predictive of a patient's intent to stand up;
   (3) using a microprocessor to compare monitored changes in the patient's bodily orientation to one or more internal positioning model(s) that are programmed inside of the microprocessor;
   (4) announcing, with the PMAA device, a verbal warning message to the patient when the monitored changes match the one or more internal positioning model(s); and then telling, with the PMAA device, the patient to "not stand up" and/or to "sit (or lie) back down"; and
   (5) simultaneously along with step (4), transmitting one or more caregiver alert signals to a Caregiver's Personal Alarm Device (CPAD), thereby alerting the caregiver that the patient is starting to stand up; and then
   (6) the caregiver subsequently intervenes with the patient to discourage the patient from standing up and possibly falling down; and
   (7) repeatably playing the verbal warning message in step (4) at an increasingly louder volume each time the message is announced when the PMAA device continues to detect ongoing changes in the patient's bodily orientation that are predictive of a patient's intent to stand up.

2. The method of claim 1, wherein the PMAA device comprises:
   a triple-axis (3D) accelerometer chip;
   a microprocessor chip;
   an inverted monostable multivibrator timing chip; and
   a digital message repeater chip.

3. The method of claim 1, wherein the PMAA device further comprises:
a triple-axis gyroscope sensor;
a message delay circuit (Lock-Out);
a battery; and
a loudspeaker.

4. The method of claim 1, wherein the PMAA device is attached to an item of clothing worn by the patient, that is selected from the group consisting of: a hat, eyeglasses, hearing aid, shirt collar, jewelry, necklace, earrings, and/or combinations thereof.

5. The PMAA system method of claim 1, wherein the PMAA device is incorporated into a smart device selected from the group consisting of: a smart phone, a smart watch, a smart fitness monitor, a smart eyeglass, and a Virtual Reality Headset, and/or combinations thereof.

6. The method of claim 1, further comprising executing a time delay line, thereby allowing a stored audio message to run its full course unimpeded when played.

7. The method of claim 1, wherein the PMAA device further comprises a 3D gyroscope for measuring changes in angular orientation of the device.

8. The method of claim 1, comprising:
wherein the electronic Patient Monitoring and Activity Alert (PMAA) device comprises a microprocessor and at least one body position-sensing sensor;
wherein the PMAA device further comprises a first antenna that transmits one or more digital alert messages via Bluetooth™ communication protocols to a second antenna that is part of the CPAD; and wherein the CPAD comprises:
a microcomputer programmed to control an LED light, a wireless communication module, a Li-ion battery and charger, and a power control switch; and
wherein the microprocessor comprises computer software that defines a "signature movement event" as comprising a coupled pair of bodily movements that comprise two sequential motions: (1) a forward rotation of a patient's upper body that positions a patient's center of gravity over his/her feet, followed by (2) a vertical movement of the patient's center of gravity when starting to stand up; and
wherein the CPAD further comprises:
a loudspeaker that announces a verbal message as an alert signal; and
a vibrating member that vibrates when the PMAA device is activated when a signature movement event is detected by the PMAA device.

9. The method of claim 1, further comprising:
(8) simultaneously, in step (5), sending the caregiver alert signal to the caregiver's CPAD each time an audio message is played in step (4).

10. The method of claim 1, wherein step (4) further comprises wirelessly transmitting the caregiver's alert signal to the CPAD from the PMAA device by using Bluetooth™ communication protocols.

11. The method of claim 1, wherein, wherein announcing the verbal warning message in step (4) comprises using one or more audio components selected from the group consisting of: a loudspeaker, headphone, audio earpiece, hearing aid, smart phone, and a smart watch, and/or combinations thereof.

12. The method of claim 1, wherein further comprising recording message(s) by using a friend, a relative, a caregiver, and/or the patient himself/herself, and/or combinations thereof, to record the verbal warning message that is stored inside the PMAA device.

13. The method of claim 1, wherein step (4) does not comprise playing an alert "beep" or "ringing" type of sound by the PMAA device.

14. The method of claim 1, wherein, further comprising activating an LED light (that is part of the CPAD) when the one or more caregiver alert signals are transmitted from the PMAA device to the CPAD in step (4).

15. The method of claim 1, wherein the PMAA device comprises a microphone that records the patient's warning message, and for sampling ambient room conditions to control the playback volume, and/or to provide audio frequency equalization.

16. The method of claim 1, further comprising double-integrating a raw accelerometer sensor data and then calculating an amount of vertical movement of the patient's body when the patient starts to stand up.

17. The method of claim 1, wherein step (4) further comprises:
recording and playing back at least three different audio messages, by the PMAA device, that escalates the message's intensity, ranging from a first "Suggestive" message, to a second "Commanding" message, to a third "Alarm" message".

18. The method of claim 1, wherein, further comprising:
(9) testing for a low-activity movement period by using the PMAA device; followed by
(10) setting the measured position sensor data equal to zero.

19. The method of claim 1, wherein further comprising performing the following steps before performing step (2), comprising:
(i) initializing the microprocessor;
(ii) calibrating one or more motion detection sensors; and
(iii) calculating one or more internal movement models that are used to compare measured bodily movements to the one or more internal movement model(s).

20. The method of claim 1, wherein, further comprising:
(a) reading a second knowledge base; and
(b) resolving this data into a plurality of different patient movement models that characterize the patient's initial intent to stand.

* * * * *